United States Patent
Kerschmann et al.

(10) Patent No.: US 6,330,348 B1
(45) Date of Patent: Dec. 11, 2001

(54) METHOD AND APPARATUS FOR MEASUREMENT OF MICROTOME PERFORMANCE

(75) Inventors: Russell L. Kerschmann; Michael E. Bolles; Andrew D. Hendrickson, all of San Francisco, CA (US)

(73) Assignee: Resolution Sciences Corporation, Corte Madera, CA (US)

( * ) Notice: Subject to any disclaimer, the term of this patent is extended or adjusted under 35 U.S.C. 154(b) by 0 days.

(21) Appl. No.: 09/235,345

(22) Filed: Jan. 21, 1999

(51) Int. Cl.[7] .................. G06K 9/00; B26D 7/08
(52) U.S. Cl. .................. 382/128; 83/915.5; 382/152
(58) Field of Search .................. 382/128, 152, 382/132, 133, 199; 83/915.5, 74; 702/34, 35

(56) References Cited

U.S. PATENT DOCUMENTS

| | | | |
|---|---|---|---|
| 3,751,780 | * 8/1973 | Villalobos | 29/65 |
| 4,618,938 | * 10/1986 | Sandland et al. | 364/552 |
| 4,741,043 | * 4/1988 | Bacus | 382/6 |
| 4,960,330 | * 10/1990 | Kerschmann | 356/36 |
| 5,241,607 | * 8/1993 | Launay et al. | 382/6 |
| 5,301,671 | * 4/1994 | Leighton et al. | 128/654 |
| 5,361,308 | * 11/1994 | Lee et al. | 382/8 |
| 5,422,730 | * 6/1995 | Barlow et al. | 356/417 |
| 5,520,182 | * 5/1996 | Leighton et al. | 128/654 |
| 5,609,083 | * 3/1997 | Persson | 83/915.5 |
| 5,625,705 | * 4/1997 | Recht | 382/128 |
| 6,007,996 | * 12/1999 | McNamara et al. | 435/6 |

OTHER PUBLICATIONS

Russ, John C., The Image Processing Handbook, second edition, CRC Press, pp. 237–238, 244, 246–247, 1995.*

* cited by examiner

*Primary Examiner*—Amelia M. Au
*Assistant Examiner*—Martin Miller
(74) *Attorney, Agent, or Firm*—Johnson & Stainbrook, LLP; Craig M. Stainbrook; Larry D. Johnson

(57) ABSTRACT

A method and apparatus for monitoring and evaluating the performance and condition of histology laboratory microtomes and microtome accessories including knives, motor drives, and illumination devices. Irregularities in an image of the surface of a block mounted on the microtome are detected and characterized, the block having been subjected to mechanical sectioning by the microtome to produce a cut block face. The image of light reflected from the surface of the block, either specular or non-specular, is recorded and subjected to graphical analysis to extract, quantify, and interpret patterned features, including those indicating anomalies in the function of the microtome, its accessories, or the tissue block itself.

4 Claims, 2 Drawing Sheets

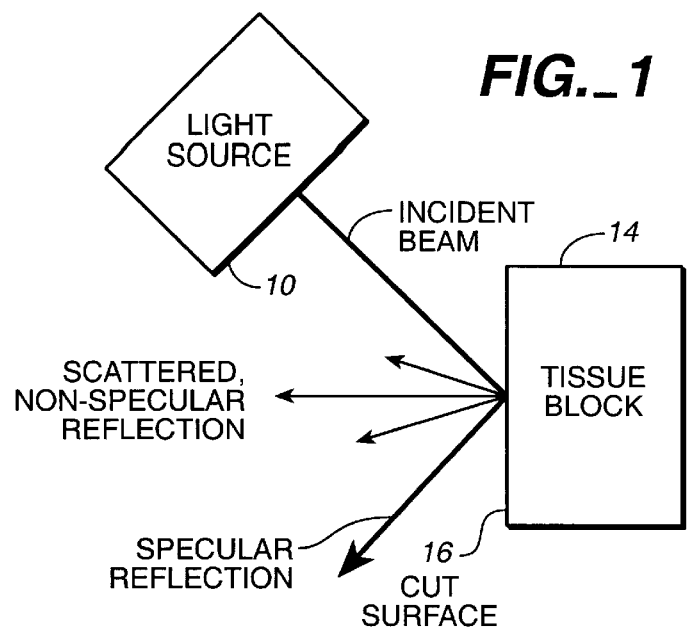
FIG._1
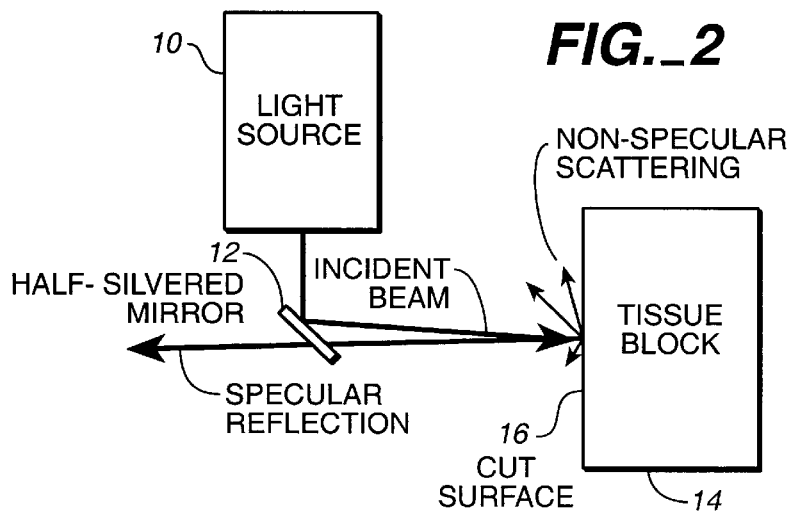
FIG._2
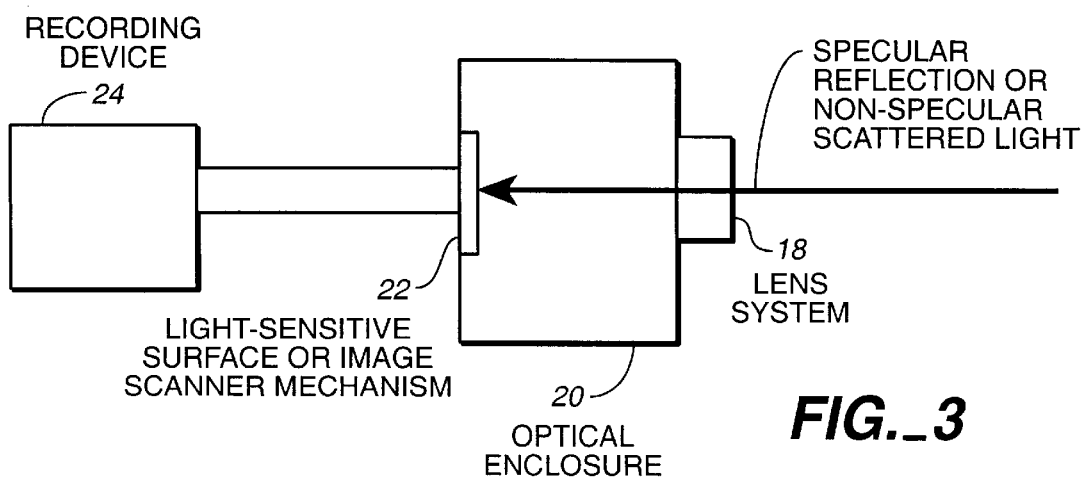
FIG._3

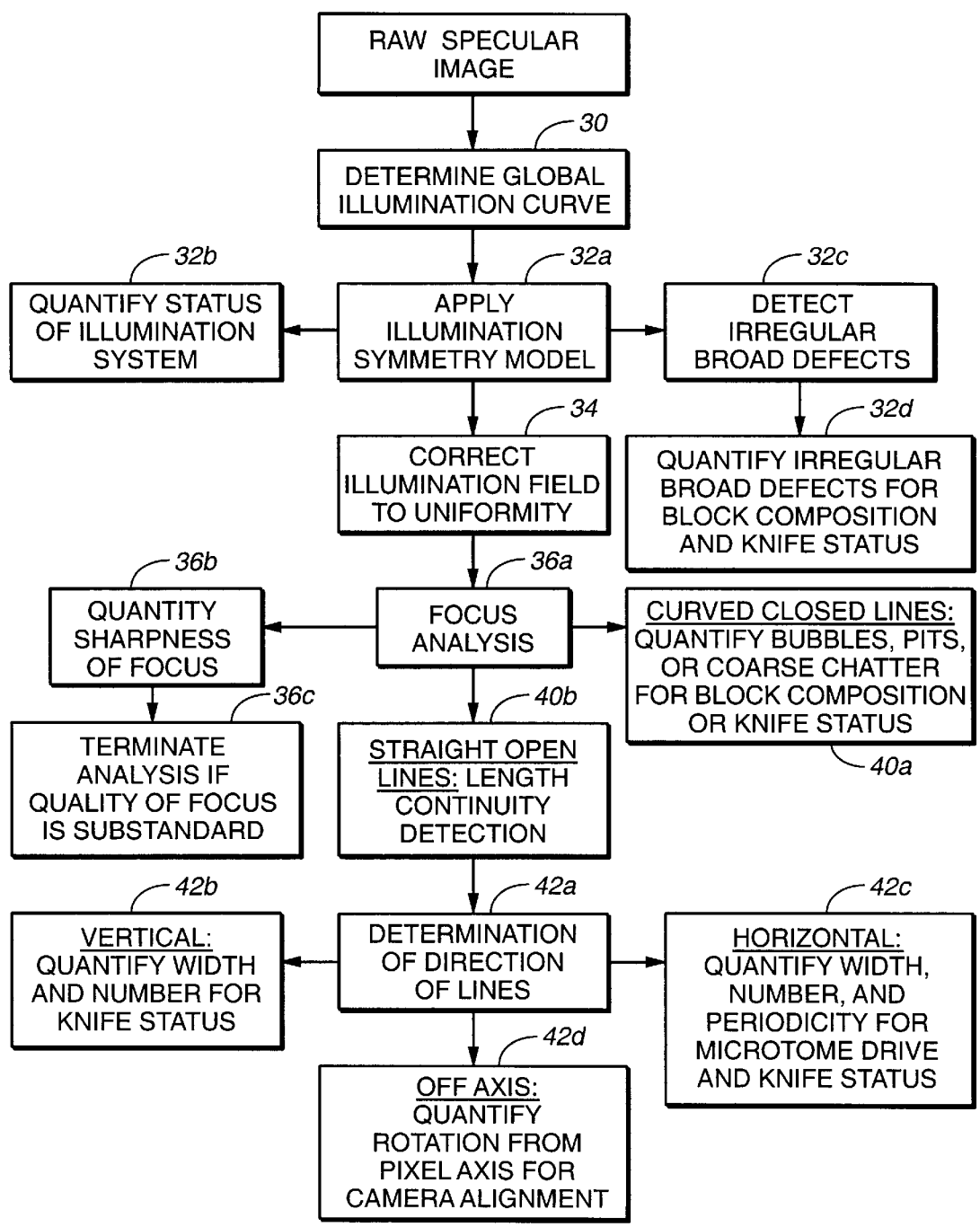
FIG._4

METHOD AND APPARATUS FOR MEASUREMENT OF MICROTOME PERFORMANCE

BACKGROUND OF THE INVENTION

1. Field of the Invention

The present invention relates generally to sectioning histology tissue samples using a microtome, and more particularly to a method and apparatus for measuring and evaluating the performance of histology laboratory microtomes and microtome accessories.

2. Description of the Prior Art

Definitions: As used herein, the term "microtome" refers to a device in which a block of sample or tissue is precisely cut such that a very thin layer of material is removed, or "sectioned" from the surface of the block. The term "microtomy" applies to the functioning of the microtome. While microtomes have been developed in a wide variety of configurations, most modern devices are arranged such that the block is fixed to one end of a vertically moveable arm and is engaged with a stationary blade; therefore, the term "vertical markings" applies to linear features aligned parallel to the motion of the block, and the term "horizontal markings" applies to linear features aligned in a direction perpendicular to the motion of the block, and parallel to the edge of the microtome blade.

The term "block face microscope" refers to a device, such as that described in U.S. Pat. No. 4,960,330, that produces microscopic images of samples by recording the face of a block in which the samples are embedded, rather than recording from the sections after they are cut from the block. The term "reflected light" refers to light incident to a surface that is returned in a specular, or mirror-like manner, rather than being scattered diffusely or absorbed and reemitted at a different wavelength, as in the case of fluorescence or phosphorescence.

The term "chatter" refers to chips in the surface of a block, sometimes randomly arranged, but often forming a series of "venetian-blind"-like periodic, parallel horizontal markings that are of a microscopic scale. Alternatively, the term "washboarding" refers to similar repeating horizontal markings that are of a sufficiently long period to be visible to the naked eye.

Artifacts of conventional microtomy: In present day practice the histologic preparation of organic tissue samples and other material for microscopy, both optical and electron microscopy, is normally carried out by infiltrating and embedding a sample in a solid block of material; cutting thin sections from the block on a microtome; placing the sections on a solid support such as a glass slide or metal grid; and staining the sections prior to examination through a microscope. Alternatively, the cut face of the block itself may be imaged by block face microscopy, obviating the need for the prepared individual sections.

In either technique, the quality of the visual information that results is influenced by several factors related to the function of the microtome and its accessories, including: 1) the mechanical state of the microtome core mechanism; 2) the status of the microtome knife; 3) in the case of motorized microtomes, the performance and state of adjustment of the drive components; 4) the configuration and composition of the block; and 5) in the case of block face microscopy, the state of the light source illuminating the block.

Block and section artifacts arising within the microtome mechanism: Improper adjustment or mechanical deterioration of the microtome mechanism may result in vibration, backlash, or other loss of precision that will degrade the quality of histologic sections and, correspondingly, may produce detectable deviations from a perfectly flat surface on the face of the block.

If the clamp that holds the block in place on the microtome is not sufficiently tightened, or if other microtome parts become loosened due to wear, an unstable block will result. This may produce an artifact referred to as "thick and thinning"; that is, the section thickness may oscillate from being too thick to too thin. Alternatively, a loose block may result in wrinkles or compression artifacts in sections, or in extreme cases the knife may "chop", penetrating deeply into the block and halting sectioning. This malfunction causes a deep horizontal marking to appear in the block face.

The speed at which the microtome is operated can have profound effects on section quality. This is especially so when cutting plastic sections using glass or diamond blades. If the velocity of the block relative to the blade is excessive, chatter may result, which in turn may damage the edge of a glass or diamond knife. Vibrations transmitted to the block due to wear or defects on cams, gears, drive screws, and other components within the core mechanism of the microtome may also produce chatter or washboarding on sections, which will be duplicated on the face of the block.

Block and section artifacts arising from the microtome knife: The microtome blade is the predominant source of artifacts in the sectioning of tissue blocks. Imperfections in the knife will result in direct damage to histologic sections and thus to the face of the block.

Knives for microtomy are made primarily from metal, glass or diamond, but other exotic materials such as sapphire have been employed. Metal knives are typically employed to section paraffin-embedded and frozen material, while glass and diamond are commonly used for cutting plastic polymer blocks, including those prepared for electron microscopy.

Microtome blades may lead to suboptimal microtome performance due to dullness, nicks, corrosion, adherence of foreign material, misalignment, as well as flaws induced in the edge of the blade during its fabrication and resharpening. Each of these defects will produce characteristic markings on the surface of the block during sectioning.

Blade dullness may result from normal wear or improper sharpening. In the case of glass knives that are not used immediately after fabrication (by controlled fracture of plate glass in the laboratory), the keenness of the edge may be lost due to gradual deformation of the glass, which over time behaves as a very slow-moving liquid. Dull blades will induce compression marks or wrinkles in sections and may cause chatter, or in the case of the softer types of embedding medium such as paraffin, may result in smearing of the tissue both in the section and on the block face. Sections cut with a dull blade may not form themselves into continuous ribbons, a desirable feature when multiple sections are to be mounted on a single glass slide.

Focal defects in the edge of the blade such as burrs, nicks, or manufacturing defects will produce vertical lines in the block face, as well as corresponding scratches in sections. If severe, such flaws may lead to shredding of sections.

Histologic section quality is highly dependent as well upon the orientation of the knife relative to the block face, and in particular to the "clearance angle"—that angle produced between the surface of the edge of the blade closest to the block and the plane of the block face. A misaligned knife blade will cause a variety of artifacts, including irregular, skipped, or excessively thick or thin sections. Too little tilt on the blade can cause the section to adhere to the block face as it passes by the knife on the return stroke instead of separating cleanly. In contrast, an excessive blade angle can result in a washboarding artifact.

In addition to these problems, embedding material, especially paraffin, may build up on the edge of the knife, causing vertical markings on the section and on the block face.

Artifacts seen in motorized microtomes: In the case of motorized microtomes, vibration originating in the motor may be transmitted to the tissue block, producing periodic or non-periodic lines on the block face during sectioning. If stepper motors are used to power the microtome, a regular pattern of straight horizontal lines may appear on the section and block face. This is a reflection of the non-continuous nature of the force produced by these types of motor drives, as well as vibrations originating in the motor which might be transmitted to the block via the microtome chassis. Various components of the drive chain, such as toothed gears and belts may introduce further vibrations.

Artifacts due to the composition and configuration of the block: The material from which the block is made and its shape and orientation significantly influence section quality. Blocks are subject to wide variations in composition that may profoundly effect their cutting characteristics. Commercial paraffin embedding material is produced in standard formulations containing organic polymers that facilitate smooth sectioning and thereby minimize cutting artifacts. However, if the paraffin is too hot during infiltration and embedding, dry or incomplete sections may result. Suboptimal processing of tissue will cause sections to have irregular holes, which appear on the block face as dull areas. Further, paraffin-based materials are quite sensitive to environmental conditions such as humidity and temperature, significant variations in which may occur in histology laboratories. Too warm an environment can lead to smearing of the surface of the block during sectioning, and occasionally technicians will apply a wet cloth or ice to the face of paraffin blocks during cutting to improve section quality.

Plastic embedding media is subject to a separate set of problems. Polymer that has exceeded its "pot life" may not polymerize completely, resulting in soft blocks and thick and thin cutting. If the components for the polymer are not apportioned correctly, soft blocks may also result, or conversely the blocks may be too brittle, which will often result in diffuse chatter. Bubbles or foreign material in the medium will result in focal defects in sections and on the face of the block.

When the cut surface of a block face transects embedded, poorly infiltrated tissues, the sample itself may cause scattering of incident light, and thus produce an image of the tissue. This is most likely to occur when there is a large differential in the hardness of the sample in comparison to the embedding material, such as when very fibrotic tissue is embedded in paraffin.

The rotational angle at which the block is mounted on the microtome is an important factor in determining section quality. Normally, microtomists strive to obtain a block with a cleanly rectangular or trapezoidal face, and to position it on the microtome such that the straight lower border of the block is parallel to the knife-edge. Improperly oriented blocks can display chatter, or in the case of paraffin sectioning may produce curved section ribbons.

Improper Adjustment of the block illumination source: In block face microscopy, the face of the block is often illuminated through epiillumination optics, wherein the same optical path is used to light the block and also to gather an image of the specimen. The epiillumination light source is most commonly of the mercury vapor, xenon, or laser type. Optimally, the sample is illuminated such that the light is delivered in a uniform field; but in routine use there are "hot spots" and a drop-off in brightness near the margins of the block face. As the light source ages, the intensity and pattern of illumination change, providing a measure of the remaining life of the bulb.

Categories of Histologic Section Defects: Defects produced on histologic sections or on the face of the tissue block fall into four categories: 1) geometrically straight vertical lines, mainly caused by scoring due to small imperfections in the edge of the microtome knife; 2) geometrically straight horizontal lines, indicating transient excursions of the knife edge deeper into the block caused by vibrations transmitted from sources outside the microtome core mechanism such as a stepper motor drive; 3) geometrically irregular lines that are usually horizontal, for example chatter, stemming from a variety of causes; and 4) random and irregular markings including bubbles, chips, patches of poorly sectioned block caused by inadequate sample infiltration, irregularities in the illumination field, or outlines of the tissue sample itself.

Current methods for assessing microtome sectioning quality: Although microtomy is over 150 years old, there exists no formalized method for real-time, quantitative monitoring of the operating condition of microtomes. The quality of sections is assessed in a gross way by examining them directly as they are cut, or through the microscope after they have been mounted and stained. Alternatively, the knife blade may be removed from the microtome and examined for flaws under a microscope using low-power magnification.

Prior art devices do not direct attention to the block face, rather than to the sections, for clues to the cause of poor quality microtome performance. This is due in most cases to the poor visibility of the surface of the rather translucent materials from which histology blocks are made, and to the fact that most flaws are microscopic. However, blocks form a very smooth surface once they have been "faced" or initially sectioned, and this feature allows for a very sensitive examination of imperfections produced by faulty microtome systems. Prior art methods and devices do not exploit this feature of sectioned histology blocks in assessing microtome performance. It would therefore be desirable to have a method and apparatus capable of using the block face to provide an immediate assessment and measurement of the operation and condition of microtomes and microtome accessories.

SUMMARY OF THE INVENTION

The present invention provides a method and apparatus for monitoring and evaluating the performance and condition of histology laboratory microtomes and microtome accessories including knives, motor drives, and illumination devices. After a histology block has been mechanically sectioned on a microtome to produce a cut block face, irregularities in an image of the surface of the block mounted on the microtome are detected and characterized. The image of light reflected from the surface of the block (either the specular or non-specular, scattered light) is recorded and subjected to graphical analysis to extract, quantify, and interpret patterned features, including those indicating anomalies in the function of the microtome, its accessories, or the tissue block itself.

The present invention comprises means for producing an image or images of the surface of a histology block after it has been cut on a microtome to remove a section; a means for recording said image or images; and a method of interpreting said image or images in order to extract information concerning the performance of the microtome and its accessories.

The invention includes a means for illuminating the surface of the block in such a manner that a specular, or mirror-like reflection is produced, along with non-specular or scattered light. In the preferred mode of operation, the specular image of this reflection is recorded and subjected to analysis, preferably by a computer equipped to process graphic images. Alternatively, the non-specular (scattered light) image of the block face may be recorded and subjected to analysis. The patterns of imperfections represented in the image are processed to extract a series of sensitive indicators of deviations from the ideal operation of the microtome.

Computational operations that may be performed on the images include: 1) edge detection by Laplacian, Sobel, or standard morphology operators to mathematically characterize any lines, including a precise determination of their exact number, angles, and the proportional area of the block face they occupy (should the markings be periodic, the analysis should detect this attribute and determine the frequency and amplitude of the pattern); 2) detection of more amorphous and random defects by employing fractal analysis and shape-fitting operators; and 3) measurement of the contour of the field illumination by using a gradient operator to determine the location of the point of maximum brightness and, by polynomial fitting, generating a function that accurately describes any anomalies in the illumination pathway.

BRIEF DESCRIPTION OF THE DRAWINGS

FIG. 1 illustrates the general means for producing an image of the cut surface of a tissue block after the block has been cut on a microtome. More particularly, FIG. 1 is a schematic view of that part of the present invention for producing an image from the cut surface of a tissue sample histology block, illustrating a light source and a tissue block.

FIG. 2 illustrates the preferred configuration of the general schematic view of FIG. 1, showing the specular image capture mode. The view shows an illumination source, a partially reflective (half-silvered) mirror, and a tissue block.

FIG. 3 is a schematic view of a means for recording the specular reflection from the tissue block face, illustrating a lens system, an optical enclosure with a light sensitive surface or image scanner mechanism for converting the image to electrical signals, and a recording device.

FIG. 4 is a flow chart illustrating the computational operations that may be performed to interpret the reflected image and to extract information concerning the operating performance of a microtome and certain of its accessories.

DETAILED DESCRIPTION OF A PREFERRED EMBODIMENT

FIG. 1 is a schematic view of that part of the present invention for producing an image from the cut surface of a tissue sample histology block, illustrating a light source 10 and a tissue block 14, each as well known in the art. Light produced at the light source is directed onto the cut surface 16 of the tissue block, and thereafter from the cut face of the tissue block in a specular and/or non-specular manner.

FIG. 2 illustrates the preferred configuration depicting that part of the present invention for producing an image from the cut surface of a tissue sample histology block as more generally illustrated in FIG. 1. FIG. 2 depicts the specular image capture mode, illustrating a light source 10, partially reflective mirror 12, and tissue block 14, all as well known in the art. Light produced at the light source is reflected from the partially reflective mirror 12 onto the cut surface 16 of the tissue block, and thereafter from the cut face of the tissue block in a specular and/or non-specular manner. The partially reflective mirror 12 allows for the illumination optics and the imaging optics to share the same elements.

A light source 10, preferably including a precisely regulated mercury vapor or xenon bulb, is positioned to project a beam of light onto a partially reflective mirror 12, which is positioned to reflect the incident beam of light onto the cut face 16 of a tissue block 14. The face of the block is illuminated in such a way that the resulting image is entirely due to the specular reflection of light from the block's surface, and not to any other source, such as fluorochrome emission originating from a sample embedded within the block.

FIG. 3 is a schematic view of that part of the present invention which is a means for recording either the specular reflection from the tissue block face or the non-specular, scattered light reflected from the tissue block face, illustrating a lens system 18, an optical enclosure 20 with a light sensitive surface or image scanner mechanism 22, for converting the specular reflection to electrical signals, preferably digital electrical signals, and a recording device 24, all of which are well known in the art.

The specular reflection or the non-specular, scattered light from the cut surface of the sample tissue block 14 is acquired by positioning a system of lenses 18, preferably high quality microscope lenses, such that they intercept the reflected image of the face of the block and sharply focus the image onto a light-sensitive planar surface (an "area array") 22, preferably a charge-coupled device (CCD) imaging chip of a high-resolution digital camera. Alternatively, a linear array may be employed, such array comprising either a single or a relatively small number of one-dimensional strips of light-sensitive elements scanned across the object to form an image, thus forming a digital image by sequentially recording a series of closely spaced parallel lines of pixels, proceeding across the image. In either embodiment, the light sensitive surface is located within an optical enclosure 20, such as a camera body. The resulting data image is then transferred to a recording device 24, such as magnetic tape or optical disk, and is then transferred for analysis, preferably by a digital computer.

Any irregularities in the cut surface 16 of the sample tissue block 14 will result in non-specular scattering of the light at those locations, resulting in a dark spot at the corresponding locus in the collected image. The optical elements are preferably aligned so that the optical axis is oriented orthogonally to the surface of the block, making the illumination pathway and the imaging pathway coincident into a single optical system, i.e., epiilumination optics.

FIG. 4 is a flow chart illustrating that part of the present invention which comprises means to perform computational operations to interpret the reflected image and to extract information concerning the operating performance of a microtome and certain of its accessories. Any detectable deviation from a perfectly uniform, flat image is considered a measurable departure from the ideal performance of the microtome and its accessories. The image is processed through a series of transformations which isolate and quantify the various classes of anomalies.

The first operation involves detection of global intensity characteristics for the evaluation of the status of the illumination system and the presence of large, amorphous defects on the block face 30. This information is further applied to a correction mask that adjusts the image and produces a uniform background intensity against which lines, pits, and other more distinct features are next distinguished 32a. After application of the correction mask, the illumination system is assessed 32b, and any detected irregular broad defects are quantified to assess block composition and knife status 32c–d. The illumination field is next corrected to uniformity 34.

Next, an operation is performed to determine if the image is in the proper focus to yield sufficient information 36a. Sharpness of focus is then quantified 36b, and analysis is terminated if the quality of focus is substandard 36c. If the image is properly focused, then an edge detection routine 38 is applied to create a binary map that indicates where edges of any surface imperfections are located. Various methods can be utilized to achieve this result, including but not restricted to Laplacian, Sobel, Frei, and Chen techniques. The binary map is further processed using next neighbor search to detect continuous lines that are categorized by shape and length 40a–b. Curved, closed lines denoting defects in the block, such as pits and bubbles, are interpreted and categorized by a curve-fitting routine 40a. Straight lines are classified on the basis of their orientations into horizontal and vertical types, as well as on the basis of their thickness 40b. Straight lines not fitting these categories are analyzed to yield respective information on alignment variations in the image recording system and/or to indicate deviations from flatness of focus 42a. Operations are then performed to quantify the width and number of vertical lines for knife operation assessment 42b, and to quantify the width, number, and periodicity of horizontal lines to assess the operation of the microtome drive and the knife 42c. The angles of lines relative to the rows and columns of pixel elements that form the image are then quantified as a measure of the rotational alignment of the camera 42d.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. An apparatus for imaging and interpreting the image of the cut surface on a histology tissue sample block in order to monitor and evaluate the condition and performance of a microtome and microtome components, said apparatus comprising:

image-producing means for producing an image of the cut surface on a histology tissue sample block;

recording means for recording the image produced; and interpretation means for interpreting the image to extract information concerning the condition and performance of the mictrotome and its components, wherein said interpreting means includes a digital computer that performs computational operations to interpret the image produced by said image producing means, and wherein said computational operations include the following:

a) detection of global intensity characteristics for evaluation of the status of the microtome illumination system and the presence of large, amorphous defects on the histology tissue sample block face;

b) application of a correction mask that adjusts the image and produces a uniform background intensity against which lines, pits, and other more distinct features are distinguished;

c) assessment of the illumination system to detect irregular broad defects and to quantify and assess block composition and knife status;

d) correction of the illumination field to uniformity;

e) determination of whether the image is in the proper focus to yield sufficient information, sharpness of focus quantification, and termination of analysis if the quality of focus is substandard;

f) if the image is properly focused, then application of an edge detection routine to create a binary map that indicates where edges of any surface imperfections are located;

g) processing of the binary map by using next neighbor search to detect continuous lines that are categorized by shape and length; curved, closed lines denoting defects in the block, such as pits and bubbles, are interpreted and categorized by a curve-fitting routine; straight lines are classified on the basis of their orientations into horizontal and vertical types; straight lines not fitting these two categories are analyzed to yield information on alignment variations in the image recording system and/or to indicate deviations from flatness of focus;

h) quantification of the width and number of vertical lines for knife operation assessment;

i) quantification of the width, number, and periodicity of horizontal lines to assess the operation of the microtome drive and the knife;

j) quantification of any lines rotated off from the pixel axis to assess camera alignment.

2. The apparatus for the monitoring and evaluation of the condition and performance of a microtome and microtome components of claim 1 wherein said edge detection routine is a Laplacian, Sobel, Frei, or Chen technique.

3. An apparatus for imaging and interpreting the image of the cut surface on a histology tissue sample block in order to monitor and evaluate the condition and performance of a microtome and microtome components, said apparatus comprising:

image-producing means for producing an image of the cut surface on a histology tissue sample block;

recording means for recording the image produced;

a digital computer that performs computational operations to interpret the image produced by said image producing means to extract information concerning the condition and performance of the mictrotome and its components, wherein said computational operations include the following:

a) detection of global intensity characteristics for evaluation of the status of the microtome illumination system and the presence of large, amorphous defects on the histology tissue sample block face;

b) application of a correction mask that adjusts the image and produces a uniform background intensity against which lines, pits, and other more distinct features are distinguished;

c) assessment of the illumination system to detect irregular broad defects and to quantify and assess block composition and knife status;

d) correction of the illumination field to uniformity;

e) determination of whether the image is in the proper focus to yield sufficient information, sharpness of focus quantification, and termination of analysis if the quality of focus is substandard;

f) if the image is properly focused, then application of an edge detection routine to create a binary map that indicates where edges of any surface imperfections are located;

g) processing of the binary map by using next neighbor search to detect continuous lines that are categorized by shape and length; curved, closed lines denoting defects in the block, such as pits and bubbles, are interpreted and categorized by a curve-fitting routine; straight lines are classified on the basis of their orientations into horizontal and vertical types; straight lines not fitting these two categories are analyzed to yield information on alignment variations in the image recording system and/or to indicate deviations from flatness of focus;

h) quantification of the width and number of vertical lines for knife operation assessment;

i) quantification of the width, number, and periodicity of horizontal lines to assess the operation of the microtome drive and the knife;

j) quantification of any lines rotated off from the pixel axis to assess camera alignment.

4. A method for monitoring and evaluating the condition and performance of a microtome and microtome components, said method comprising the steps of:

producing an optical image of the cut surface of a histology tissue sample block sectioned by the microtome by using a partially reflective mirror to reflect and direct onto the cut face on the histology tissue sample block an incident beam of light originating from either a mercury vapor or xenon bulb;

intercepting the optical image formed by any specular reflection from the cut surface on said histology tissue sample block and directing said image through a system of microscope lenses onto a light-sensitive planar surface, such as a charge-coupled imaging chip;

converting said optical image of the cut surface of the histology tissue sample block into a digital electronic image;

recording said digital electronic image onto a suitable recording medium, such as magnetic tape or optical disk;

interpreting said digital image using a digital computer to extract information concerning the condition and performance of the microtome and its components;

using a suitably programmed digital computer to determine whether the image of the cut surface of the histology tissue sample block is in the proper focus to yield sufficient information, sharpness of focus quantification, and to terminate image analysis if the quality of focus is substandard;

using said digital computer, if the image is properly focused, to apply an edge detection operation, such as a Laplacian, Sobel, Frei, or Chen technique, to create a binary map that indicates where edges of any surface imperfections are located;

processing said binary map by using next neighbor search to detect continuous lines that are categorized by shape and length; using a curve-fitting routine to interpret and categorize curved, closed lines denoting defects in the block, such as pits and bubbles; classifying straight lines on the basis of their orientations into horizontal and vertical types; analyzing straight lines not fitting these two categories to yield information on alignment variations in the image recording system and/or to indicate deviations from flatness of focus.

* * * * *